(12) United States Patent
Nishigishi

(10) Patent No.: US 9,039,754 B2
(45) Date of Patent: May 26, 2015

(54) STENT

(75) Inventor: Makoto Nishigishi, Seto (JP)

(73) Assignee: ASAHI INTECC CO., LTD., Nagoya-shi (JP)

( * ) Notice: Subject to any disclaimer, the term of this patent is extended or adjusted under 35 U.S.C. 154(b) by 150 days.

(21) Appl. No.: 13/438,391

(22) Filed: Apr. 3, 2012

(65) Prior Publication Data

US 2012/0265294 A1    Oct. 18, 2012

(30) Foreign Application Priority Data

Apr. 14, 2011    (JP) .................. 2011-090495

(51) Int. Cl.
*A61F 2/06*    (2013.01)
*A61F 2/90*    (2013.01)

(52) U.S. Cl.
CPC ............. *A61F 2/90* (2013.01); *A61F 2002/068* (2013.01); *A61F 2250/0017* (2013.01); *A61F 2250/0036* (2013.01); *A61F 2250/0039* (2013.01)

(58) Field of Classification Search
CPC ................ A61F 2250/0017; A61F 2250/0036; A61F 2250/0039
USPC ...................... 623/1.15, 1.22, 1.32, 1.49, 1.51
See application file for complete search history.

(56) References Cited

U.S. PATENT DOCUMENTS

| 6,719,934 | B2 | 4/2004 | Stinson | |
|---|---|---|---|---|
| 2002/0179166 | A1* | 12/2002 | Houston et al. | 138/39 |
| 2006/0184238 | A1* | 8/2006 | Kaufmann et al. | 623/1.53 |
| 2010/0114304 | A1* | 5/2010 | Craig | 623/1.49 |

FOREIGN PATENT DOCUMENTS

| CN | 1455657 | 11/2003 |
|---|---|---|
| CN | A-101472536 | 7/2009 |
| GB | 2 470 484 A | 11/2010 |
| JP | A-11-057021 | 3/1999 |
| JP | A-2007-518520 | 7/2007 |
| WO | WO 02/05729 A2 | 1/2002 |
| WO | WO 2005/072653 A1 | 8/2005 |
| WO | WO 2007/139699 A2 | 12/2007 |
| WO | WO 2010/120926 A1 | 10/2010 |
| WO | WO 2010120926 A1 * | 10/2010 |
| WO | WO 2010/135433 A1 | 11/2010 |

OTHER PUBLICATIONS

Jul. 20, 2012 Search Report issued in European Patent Application No. 12163278.0.
Jul. 12, 2013 Office Action issued in European Patent Application No. 12163278.0.
Sep. 22, 2014 Notice of Reasons for Rejection issued Japanese Patent Application No. JP2011-090495 (with English translation).
Aug. 27, 2014 First Office Action issued in Chinese Patent Application No. 201210091196.0 (with English translation).

* cited by examiner

*Primary Examiner* — Kathleen Holwerda
*Assistant Examiner* — Sarah Simpson
(74) *Attorney, Agent, or Firm* — Oliff PLC

(57) ABSTRACT

A stent, having a central axis that extends in a longitudinal direction of the stent, includes a first strand group and a second strand group. The first strand group and the second strand group are woven together. The first strand group is wound in a right-handed spiral around the central axis and the second strand group is wound in a left-handed spiral around the central axis. A maximum diameter of first strands constituting the first strand group is different from a maximum diameter of second strands constituting the second strand group.

2 Claims, 4 Drawing Sheets

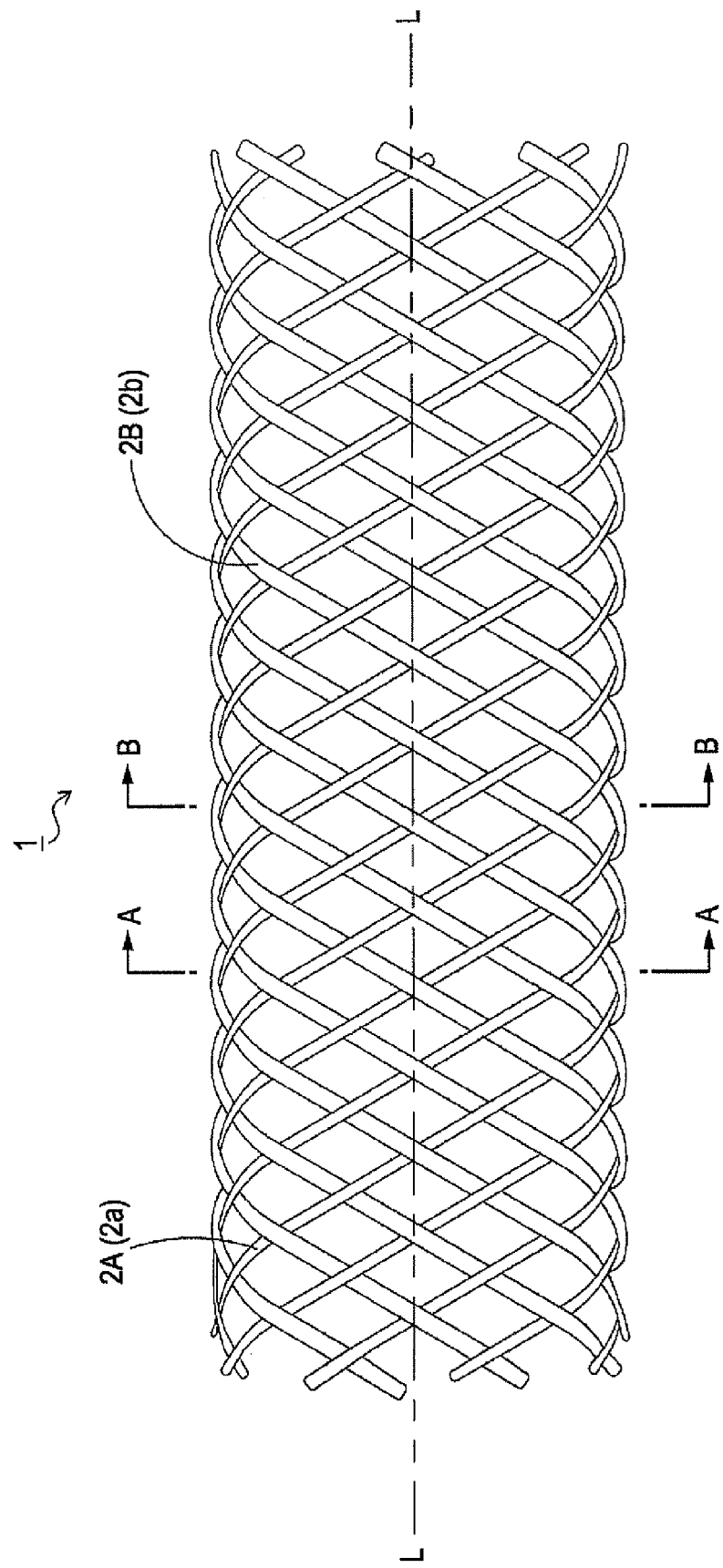

STENT

CROSS REFERENCE TO RELATED APPLICATIONS

This application claims priority to Japanese Patent Application No. 2011-090495 filed with the Japan Patent Office on Apr. 14, 2011, the entire content of which is hereby incorporated by reference.

TECHNICAL FIELD

The disclosed embodiments relate to a medical device. More specifically, the disclosed embodiments relate to a stent.

BACKGROUND

A stent is a medical instrument used to restore or suppress the bloodstream. The stent is indwelt in, for example, a stenosis in a vessel. The indwelt stent restores the bloodstream by keeping the inner diameter of the stenosis in the vessel constant. Alternatively, the stent is indwelt at an inlet of an aneurysm. The indwelt stent suppresses the bloodstream flowing into the aneurysm.

Such a stent is disclosed in, for example, JP-A-11-57021, U.S. Pat. No. 6,719,934B2 or JP-A-2007-518520. The stent disclosed in the patent document is in the shape of a cylindrical basket. That is, this stent is formed by weaving a plurality of strands together.

SUMMARY

The diameter of a stent in the related art disclosed in JP-A-11-57021 may be set to an arbitrary value. Therefore, the stent may be indwelt in a lesion site.

However, the stent in the related art disclosed in the above patent document exhibits operational problems. That is, the related art stent indwelt at a lesion site is hardly effective for stabilizing the bloodstream inside an inner cavity of the stent (hereinafter also referred to as stent inner-cavity bloodstream). For example, the related art stent indwelt at an inlet of an aneurysm cannot fully suppress the bloodstream flowing into the aneurysm.

The present inventor has conducted various studies to address the above problems. As a result, the present inventor has made the stent according to the disclosed embodiments of the present invention, in which the stent inner-cavity bloodstream is stabilized by spiral grooves formed on the inner surface of the stent.

That is, a stent according to an embodiment of the present invention includes a first strand group and a second strand group which are woven together, wherein the first strand group is wound in a right-handed spiral around a virtual central axis that extends in a longitudinal direction of the stent, the second strand group is wound in a left-handed spiral around the virtual central axis, and a maximum diameter of a first strand constituting the first strand group is substantially different from a maximum diameter of a second strand constituting the second strand group.

Generally, the "maximum diameter" corresponds to a maximum linear extension of the cross-sectional area of the respective one of the first and second strand, i.e., in analogy to the so-called Feret-diameter, to a longest distance between any two points on the contour of the cross-sectional area of the respective one of the first and second strand. Thus, where the respective one of the first and second strand has a circular cross-sectional area, the "maximum diameter" corresponds to the diameter of the contour of the circular cross-sectional area of the respective one of the first and second strand, and where the respective one of the first and second strand has a non-circular sectional area, the "maximum diameter" corresponds to the diameter of a circle surrounding the contour of the non-circular cross-sectional area of the respective one of the first and second strand.

Further, among the plurality of first strand constituting the first strand group the diameter of one of the first strand may be different to or may be the same as the diameter of another one of the first strand, as long as each of the first strand has a smaller diameter than each of the second strand. Specifically, the first strand may each have a same (first) diameter, or the diameter may vary among the first strand. Similarly, among the plurality of second strand constituting the second strand group the diameter of one of the second strand may be different to or may be the same as the diameter of another one of the second strand, as long as each of the second strand has a larger diameter than each of the first strand. Specifically, the second strand may each have a same (second) diameter, or the diameter may vary among the second strand.

The stent according to an embodiment of the present invention preferably further includes a dense part having a larger total number of the first strands and the second strands; and a sparse part having a smaller total number of the first strands and the second strands, wherein in the sparse part, the number of strands having the smaller maximum diameter of the first strands and the second strands is substantially less than the number of strands having the larger maximum diameter of the first strands and the second strands.

In the disclosed embodiments of the present invention, preferably, the dense part is formed at both ends of the stent and the sparse part is formed at a central part of the stent.

BRIEF DESCRIPTION OF THE DRAWINGS

The foregoing and other objects, features, aspects and advantages of the invention will become more apparent from the following detailed description when taken in conjunction with the accompanying drawings.

FIG. 1 is a plan view schematically illustrating a stent according to one embodiment of the present invention;

DETAILED DESCRIPTION OF EMBODIMENTS

Figure 2A:
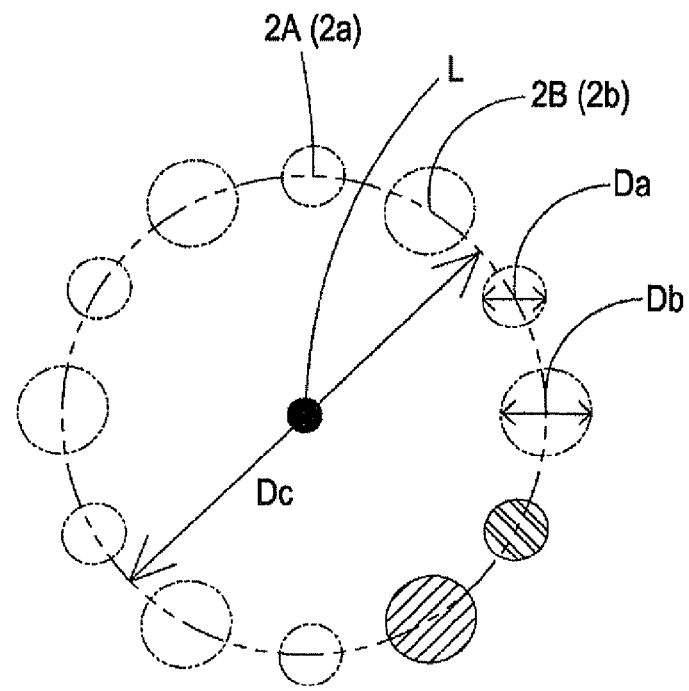
FIG. 2A is a cross-sectional view taken along line A-A of the stent shown in FIG. 1.

Preferred embodiments of the present invention are described below with reference to the accompanying drawings, in which like reference characters designate similar or identical parts throughout the several views thereof.

A stent according to one embodiment of the present invention will be described below with reference to FIGS. 1 to 3.

Figure 2B:
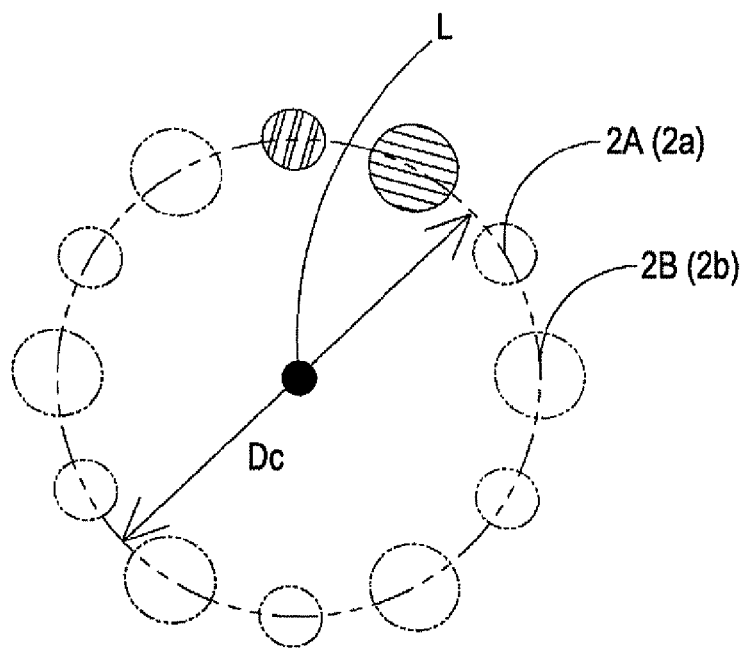
FIG. 2B is a cross-sectional view taken along line B-B of the stent shown in FIG. 1.
Figure 3:
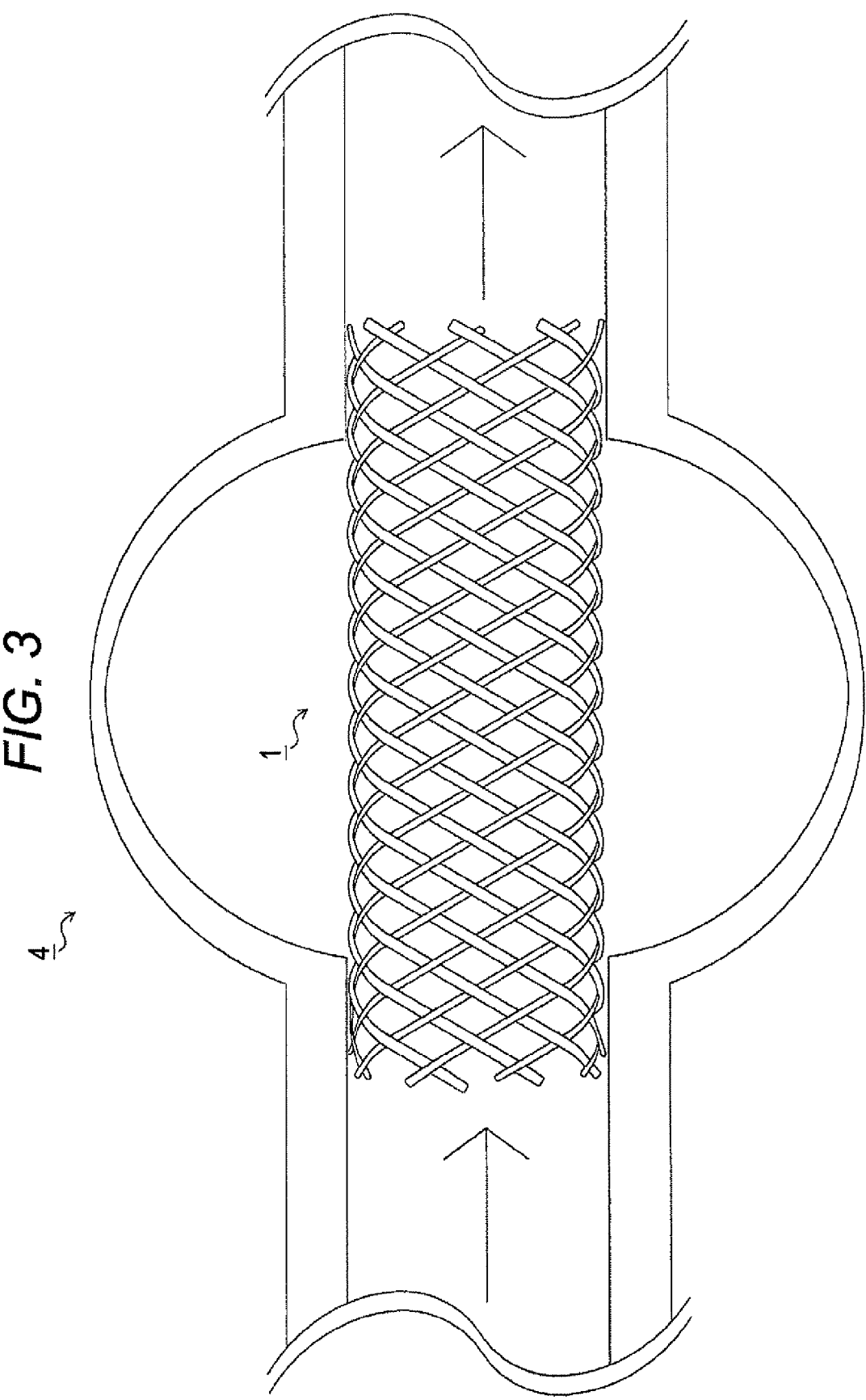
FIG. 3 is a schematic view illustrating an example of a method for using the stent illustrated in FIG. 1.

In the example illustrated in FIGS. 1 to 3, the maximum diameter of a first strand constituting a first strand group is substantially smaller than the maximum diameter of a second strand constituting a second strand group. In other words, the maximum diameter of a second strand constituting a second strand group is substantially larger than the maximum diameter of a first strand constituting a first strand group.

However, the configuration of the stent 1 is not limited to the above example as long as the maximum diameter of the first strand constituting the first strand group is substantially different from the maximum diameter of the second strand constituting the second strand group. For example, the maximum diameter of the first strand constituting first strand group may be substantially larger than the maximum diameter of the second strand constituting the second strand group.

In the description given below, the strand having the larger maximum diameter is also referred to as a thick strand. On the other hand, the strand having the smaller maximum diameter is also referred to as a thin strand.

In FIGS. 2A and 2B, only one of the first strand and the second strand is shaded for easy understanding of the relationship therebetween.

As illustrated in FIG. 1, the stent 1 includes a first strand group 2A and a second strand group 2B, which are woven together.

More specifically, the first strand group 2A is wound in a right-handed spiral around a virtual central axis L that extends in the longitudinal direction of the stent 1. The second strand group 2B, on the other hand, is wound in a left-handed spiral around the virtual central axis L.

In this manner, in the stent 1 of the present embodiment, first strands 2*a* constituting the first strand group 2A wound in a right-handed spiral and second strands 2*b* constituting the second strand group 2B wound in a left-handed spiral are woven together. Therefore, the stent 1 of the present embodiment has a sufficient strength compared to a stent where the strands are spirally wound in only one direction (i.e., either in the shape of a right-handed coil or a left-handed coil).

As illustrated in FIGS. 2A and 2B, the maximum diameter Da of the first strand 2*a* constituting the first strand group 2A is substantially different from the maximum diameter Db of the second strand 2*b* constituting the second strand group 2B.

More specifically, in the present embodiment, the maximum diameter Da of the first strand 2*a* constituting the first strand group 2A is substantially smaller than the maximum diameter Db of the second strand 2*b* constituting the second strand group 2B. That is, the maximum diameter Db of the second strand 2*b* constituting the second strand group 2B is substantially larger than the maximum diameter Da of the first strand 2*a* constituting the first strand group 2A.

The stent diameter Dc is defined as the diameter of a circle obtained by drawing a virtual curved line passing through the central axis of each first strand 2*a* and the central axis of each second strand 2*b* adjacent to the first strand 2*a*, in the stent 1 to which no external force is applied (i.e., the stent in a free state). In the cut surface of the stent 1 having the stent diameter Dc, the circumference portion of the second strand 2*b* having the larger maximum diameter protrudes toward the virtual center (virtual central axis L) more evidently than the first strand 2*a*.

That is, a left-handed spiral protrusion is formed of the circumference portion (i.e., outer peripheral portion) of the second strand 2*b* protruding toward the virtual center (virtual central axis L) more than the circumference portion (i.e., outer peripheral portion) of the first strand 2*a*. On the other hand, a right-handed spiral protrusion is formed of the circumference portion (i.e., outer peripheral portion) of the first strand 2*a* protruding toward the virtual center (virtual central axis L) less than the circumference portion (i.e., outer peripheral portion) of the second strand 2*b*. In other words, the left-handed spiral protrusion has a larger height than the right-handed spiral protrusion toward the virtual center (virtual central axis L).

As illustrated in FIG. 3, therefore, in the stent 1 indwelt at a lesion site (aneurysm 4), the second strand 2*b* (left-handed spiral protrusion) more evidently protruding toward the virtual center (virtual central axis L) functions as a left-handed spiral deflector. Therefore, the inner-cavity bloodstream of the stent 1 is turned into a left-handed spiral flow. As a result, the bloodstream is stabilized. Note that in FIG. 3, the bloodstream is shown by an arrow pointed in one direction.

With this configuration, the stent 1 indwelt at the inlet of the aneurysm 4 sufficiently suppresses the bloodstream flowing into the aneurysm 4.

As illustrated in FIG. 1, the first strand 2*a* constituting the first strand group 2A is in the shape of a rod with a circular cross section.

For example, about several to several tens of the first strands 2*a* may be used.

The material for forming the first strand 2*a* may be, for example, stainless steel; super elastic alloys such as, a Ni—Ti alloy, a Cu—Al—Ni alloy, or a Cu—Zn—Al alloy; a piano wire; tungsten; or synthetic resins such as polyester, polyurethane, polyolefin, polytetrafluoroethylene, or a silicon resin.

Examples of the stainless steel include martensite-based stainless steel, ferrite-based stainless steel, austenite-based stainless steel, austenitic-ferritic duplex stainless steel, and precipitation-hardened stainless steel.

As illustrated in FIG. 1, the second strand 2*b* constituting the second strand group 2B is in the shape of a rod with a circular cross section.

For example, about several to several tens of the second strands 2*b* may be used.

The material for the second strand 2*b* may be the same as or substantially different from that for the first strand 2*a*.

In the case where the material for the first strand 2*a* is substantially different from that for the second strand 2*b*, various characteristics of the materials for the respective strands can be exerted in combination.

The total number of the first strands 2*a* is equal to the total number of the second strands 2*b*.

Further, in the stent 1 of the present embodiment, the plurality of first strands 2*a* have each a same (first) diameter Da, and the plurality of second strands 2*b* have each a same (second) diameter Db which is different from the first diameter Da. The left-handed spiral protrusions formed by the second strands 2*b* protruding toward the virtual center (virtual central axis L) have each a larger (radial) height than the right-handed spiral protrusions formed by the first strands 2*a* protruding toward the virtual center (virtual center axis L). Especially, each height of the left-handed protrusions and each height of the right-handed protrusions is regulated to substantially uniform size. Therefore, in the stent 1 of the present embodiment indwelt at a lesion site, the bloodstream is more stabilized by being turned into a left-handed spiral flow by the left-handed protrusions functioning as a left-handed spiral deflector having substantially uniform height.

The stent 1 of the present embodiment having the above configuration is formed of the first strand group 2A and the second strand group 2B, which are woven together. Therefore, the strands constituting the respective strand groups are slidable relative to each other. That is, the diameter of the stent 1 can be set to an arbitrary value by sliding these strands. In other words, the diameter of the stent 1 can be increased or decreased, as necessary, by sliding these strands.

Therefore, in the case where the stent 1 is to be inserted into a tubular organ with an inner diameter substantially smaller than the diameter Dc of the stent 1 in the free state, the diameter Dc of the stent 1 is decreased by sliding the strands before the stent 1 is inserted into the tubular organ.

The stent of the present embodiment may be used, for example, as follows.

The diameter of the stent of the present embodiment is decreased. The stent with the decreased diameter is accommodated in a catheter. Then, the catheter is guided to, and positioned in, a lesion site along a guidewire.

After positioning the catheter, the stent is let out of the catheter and indwelt at the lesion site.

Note that the stent of the present embodiment may be guided to the lesion site using a balloon catheter.

The stent of the present embodiment may be manufactured, for example, as follows. A plurality of thin strands to constitute a first strand group and a plurality of thick strands to constitute a second strand group are prepared. Next, the plurality of thin strands is set in a stent weaving machine as right-handed spiral strands. Meanwhile, the plurality of thick strands is set in the stent weaving machine as left-handed spiral strands. After that, the stent weaving machine is operated to alternately weave the respective strands into the shape of a cylinder. As a result, a stent according to an embodiment of the present invention is obtained.

The functions and effects of the stent of the present embodiment will be described below.

In the stent of the present embodiment, the first strands wound in a right-handed spiral and the second strands wound in a left-handed spiral are woven together. Therefore, the stent of the present embodiment has a sufficient strength compared to a stent where the strands are spirally wound in only one direction (i.e., either in the shape of a right-handed coil or a left-handed coil).

A left-handed spiral protrusion formed of the second strand protruding toward the virtual central axis has a larger height than a right-handed spiral protrusion formed of the first strand protruding toward the virtual central axis.

Therefore, in the stent of the present embodiment indwelt at a lesion site, the left-handed spiral protrusion more evidently protruding toward the virtual central axis functions as a left-handed spiral deflector. As a result, the stent inner-cavity bloodstream is stabilized by being turned into a left-handed spiral flow.

A stent according to another embodiment of the present invention will be described below with reference to the drawing. The stent of the present embodiment has the same configuration as the stent of the first embodiment except for the following features. That is, the stent of the present embodiment has a dense part and a sparse part. The total number of the first and second strands in the dense part is substantially larger than that in the sparse part. Of the first strands and the second strand in the sparse part, the number of the strands having the smaller maximum diameter is substantially less than the number of the strands having the larger maximum diameter.

Therefore, the overlapping features with the stent of the first embodiment will not be described.

Figure 4:
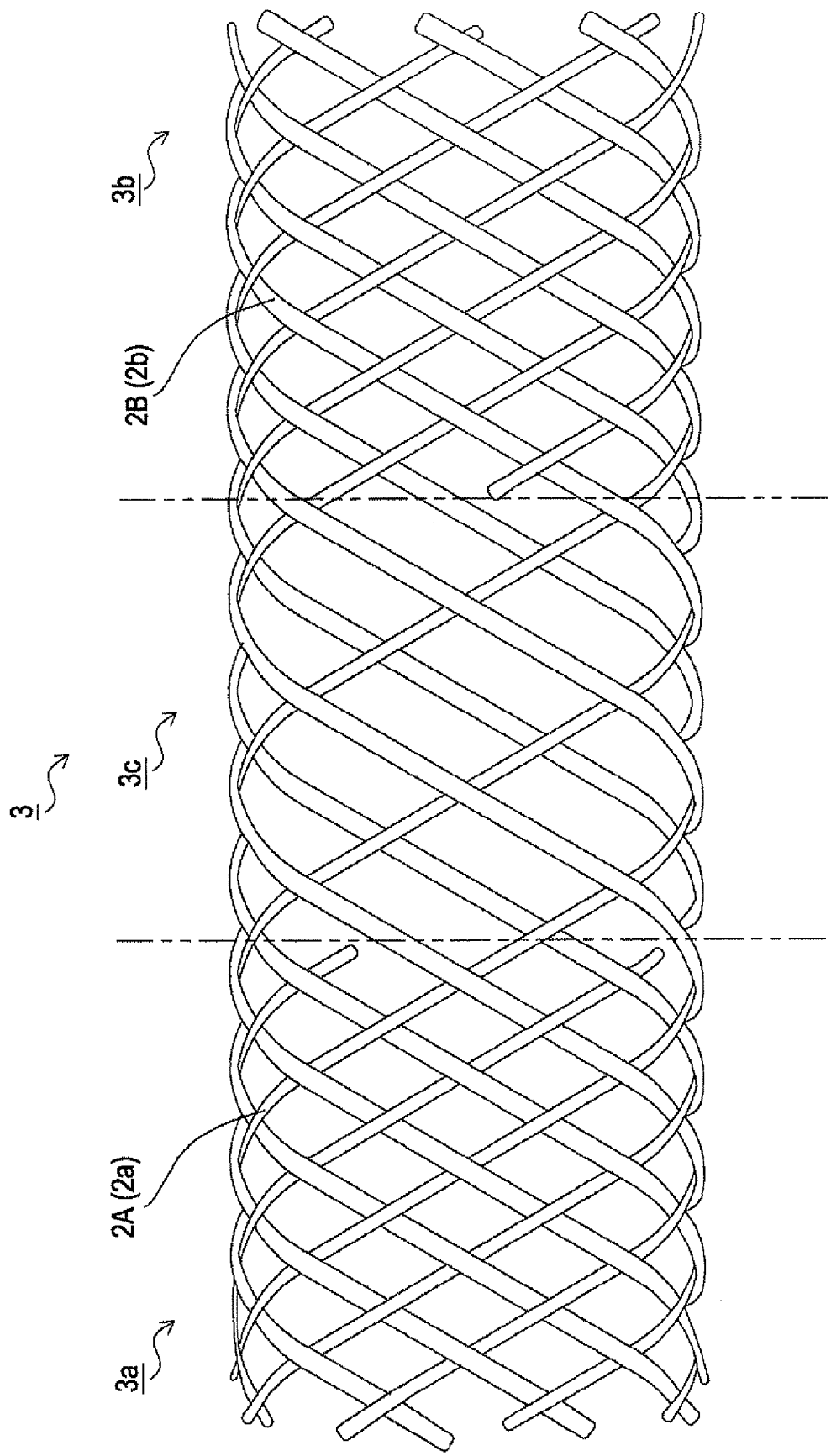
FIG. 4 is a plan view schematically illustrating a stent according to another embodiment of the present invention.

FIG. 4 is a plan view schematically illustrating the stent according to another embodiment of the present invention.

A stent 3 of the present embodiment illustrated in FIG. 4 includes dense parts 3a and 3b formed at both ends of the stent 3 in a longitudinal direction thereof, and a sparse part 3c formed in the middle of the stent 3 in a longitudinal direction thereof.

In the dense parts 3a and 3b, the total number of the first strands 2a is equal to the total number of the second strands 2b. In the sparse part 3c, the total number of the first strands 2a and the second strands 2b is substantially smaller than that in the dense parts 3a and 3b. Therefore, the dense parts 3a and 3b have a higher strength and are less likely to be deformed than the sparse part 3c.

In the dense parts 3a and 3b, for example, about several to several tens of the first strands 2a in total may be used. On the other hand, about several to several tens of the second strands 2b in total may be used.

Of the first strands 2a and the second strands 2b in the sparse part 3c, the number of the first strands 2a having the smaller maximum diameter is substantially less than the number of the second strands 2b having the larger maximum diameter.

In the sparse part 3c, therefore, the number of the left-handed spiral protrusions formed of the second strands 2b is substantially larger than the number of the right-handed spiral protrusions formed of the first strands 2a.

With this configuration, in the sparse part 3c, the protruding shape of the left-handed spiral protrusion serving as the left-handed spiral deflector is further emphasized.

The difference in total number between the first strands 2a and the second strands 2b constituting the sparse part 3c is preferably 2 to 12.

The stent of the present embodiment may be manufactured as follows, for example. That is, a stent precursor is produced in the same manner as the manufacturing method for the stent of the first embodiment. Next, only a predetermined number of the first strands in a part to be the sparse part is cut and removed. As a result, the stent according to second embodiment of the present invention is obtained.

Alternatively, the stent of the present embodiment may be manufactured as follows. That is, the stent weaving machine is used to weave the strands, thereby forming the stent in the same manner as the manufacturing method for the stent of the first embodiment. In this case, after one dense part (end part) is formed by weaving, the feeding of a predetermined number of the first strands is stopped. Next, the weaving is continued with the feeding of the first strands stopped. As a result, a sparse part (central part) is formed. After that, the feeding of the first strands that has been stopped is restarted to continue the weaving. In this manner, the other dense part (end part) is woven. As a result, the stent according to the second embodiment of the present invention is obtained.

The functions and effects of the stent of the present embodiment will be described below.

The stent of the present embodiment can exert the same functions and effects as those of the first embodiment described above, as well as the following additional functions and effects.

In the sparse part of the stent of the present embodiment, the protruding shape of the left-handed spiral protrusion serving as the left-handed spiral deflector is further emphasized.

Therefore, in the case where the stent of the present embodiment is indwelt at a lesion site, the bloodstream flows through the inner cavity of the dense part and is turned into a left-handed spiral flow. The resultant bloodstream then flows through the inner cavity of the sparse part and is turned into a stronger left-handed spiral flow. As a result, the bloodstream is even more stabilized.

The dense part, which has more first strands and second strands and is less likely to be deformed, is positioned at each end of the stent. Therefore, the stent indwelt at the lesion site is securely fixed at that position. As a result, the stent is hardly displaced.

The sparse part having a stronger deflecting effect is positioned at the central part of the stent. Therefore, the central part of the stent indwelt at an inlet of an aneurysm can easily cover the inlet of the aneurysm.

The stent indwelt in this manner makes it easy for the blood to flow along the stent. As a result, the bloodstream flowing into the aneurysm can be effectively prevented.

In the stent according to an embodiment of the present invention, the maximum diameter of the first strand constituting the first strand group may be larger than the maximum diameter of the second strand constituting the second strand group.

In the stent having such a configuration, the right-handed spiral protrusion more evidently protruding toward the virtual center (virtual central axis) functions as a right-handed spiral deflector. As a result, the inner-cavity bloodstream of the stent is turned into a right-handed spiral flow.

The stent with this configuration may also include a dense part and a sparse part as described in the second embodiment.

Of the first strand and the second strand in the stent according to an embodiment of the present invention, the ratio between the maximum diameter of the thin strand and the maximum diameter of the thick strand is preferably about 1:1.2 to about 1:3.

In the case where the ratio between the maximum diameter of the thin strand and the maximum diameter of the thick strand is in the above range, a spiral deflector is formed by the thick strand more evidently protruding toward the virtual center (virtual central axis). This spiral deflector has a shape more suitable for adjusting the flow. Therefore, the bloodstream is even more stabilized.

In this case, the maximum diameter of the thick strand is preferably about 0.024 mm to about 0.06 mm. The maximum diameter of the thin strand, on the other hand, is preferably about 0.02 mm to about 0.05 mm.

In the stent according to an embodiment of the present invention, the total number of the first strands may be equal to or substantially different from the total number of the second strands, as described in the first embodiment.

In the case where the total number of the first strands is substantially different from the total number of the second strands, the number of the thick strands is preferably larger than the number of the thin strands.

The stent having such a configuration may also include a dense part and a sparse part as described in the second embodiment.

The thick strand more evidently protrudes toward the virtual center (virtual central axis) and functions as the spiral deflector. Therefore, the more the number of such strands, the more spiral deflectors are formed. As a result, the bloodstream is further stabilized.

In the stent according to an embodiment of the present invention, the cross-sectional shape of the first strand and the second strand is not limited to circular, but may be, for example, oval or elliptic. Therefore, the "diameter" corresponds to a maximum linear extension of the cross-sectional area of the respective one of the first and second strands, i.e., in analogy to the so-called Feret-diameter, to a longest distance between any two points on the contour of the cross-sectional area of the respective one of the first and seconds strands. Where the first and second strands have each a circular cross-sectional area, the "diameter" corresponds each to the diameter of the contour of the circular cross-sectional area of the first and second strands, respectively, and where the first and second strands have each a non-circular cross-sectional area, the "diameter" corresponds each to the diameter of a circle surrounding the contour of the non-circular cross-sectional area of the first and second strands, respectively.

In the stent according to an embodiment of the present invention, the plurality of first strands constituting the first strand group may be each formed of the same material. Alternatively, the plurality of the first strands may be formed of different materials, respectively.

The plurality of second strands constituting the second strand group may be each formed of the same material. Alternatively, the plurality of the second strands may be formed of different materials, respectively.

In the stent according to an embodiment of the present invention, the plurality of first strands constituting the first strand group and/or the plurality of second strands constituting the second strand group may include strands formed of radiopaque metal (e.g., platinum, gold, and tungsten).

In this case, the stent can easily be recognized in a contrast image. Therefore, the stent can easily be positioned when indwell in a lesion site.

The outer surface of the stent according to an embodiment of the present invention may be coated with a hydrophilic material.

The hydrophilic coating reduces the sliding resistance between the stent and a delivering catheter in which the stent is accommodated. As a result, the stent can smoothly be let out of the catheter and easily indwell in a predetermined position.

The outer surface of the stent according to an embodiment of the present invention may be coated with various chemicals. Examples of the chemical include sirolimus and paclitaxel, which are used to prevent restenosis.

The stent according to an embodiment of the present invention may be used for the purpose of being indwelt at an inlet of an aneurysm. Alternatively, the stent according to an embodiment of the present invention may be used for the purpose of being indwelt in a tubular organ other than the vessel (e.g., urethra, bile duct, esophagus, intestine, and trachea).

A graft may be attached to the inner surface and/or outer surface of the stent according to an embodiment of the present invention. In this case, the stent can be used as a stent graft.

Examples of the material for the graft include at least one of polyester and PTFE.

While the disclosed embodiments have been shown and described in detail, the foregoing description is in all aspects illustrative and not restrictive. It is therefore understood that numerous modifications and variations can be devised without departing from the spirit and scope of the invention.

What is claimed is:

1. A stent having a central axis that extends in a longitudinal direction of the stent, the stent comprising:
    a first strand group having a plurality of first strands;
    a second strand group having a plurality of second strands, the first strand group and the second strand group being woven together;
    a dense part formed at both ends of the stent; and
    a sparse part formed at a central part of the stent, wherein
        the first strand group is wound in a right-handed spiral around the central axis,
        the second strand group is wound in a left-handed spiral around the central axis,
        a maximum diameter of each of the plurality of first strands constituting the first strand group is less than a maximum diameter of each of the plurality of second strands constituting the second strand group,
        in the sparse part, a number of the first strands is less than a number of the second strands, and
        at least one distalmost end of at least one of the plurality of first strands is disposed between one of the dense parts and the sparse part.

2. The stent according to claim 1, wherein
a difference between the number of the first strands and the number of the second strands in the sparse part is between 2 and 12.

* * * * *